(12) United States Patent
Hoelke et al.

(10) Patent No.: US 8,211,684 B2
(45) Date of Patent: Jul. 3, 2012

(54) STABILIZATION OF THERMOLYSIN IN AQUEOUS SOLUTION

(75) Inventors: Werner Hoelke, Penzberg (DE);
Johann-Peter Thalhofer, Weilheim (DE); Antje Liehre, Penzberg (DE);
Markus Weber, Habach (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 237 days.

(21) Appl. No.: 12/542,028

(22) Filed: Aug. 17, 2009

(65) Prior Publication Data

US 2010/0248326 A1  Sep. 30, 2010

(30) Foreign Application Priority Data

Aug. 27, 2008  (EP) .................................... 08015100

(51) Int. Cl.
*C12N 9/96* (2006.01)
*C12N 9/48* (2006.01)
(52) U.S. Cl. ....................... 435/188; 435/212
(58) Field of Classification Search .................. 435/188, 435/212
See application file for complete search history.

(56) References Cited

U.S. PATENT DOCUMENTS

2003/0078192 A1* 4/2003 Winter et al. ..................... 514/2
2004/0234944 A1* 11/2004 Quaedflieg et al. .............. 435/4

FOREIGN PATENT DOCUMENTS

EP  0640687 B1  4/2002
WO  03/088993 A1  10/2003

OTHER PUBLICATIONS

Endo, S., "Studies on Protease Produced by Themophilic Bacteria," Journal of Fermentation Technology 40:1 (1962) 346-353, Abstract only.
Feder, J. et al., "Studies on the Role of Calcium in Thermolysin," Biochemistry 10:24 (1971) 4552-4556.
Inouye, K et al., "Effect of amino acid residues at the cleavable site of substrates on the remarkable activation of thermolysin by salts," Biochem. J. 13 (1996) 133-138.
Inouye, K et al, "Extracellular production of recombinant thermolysin expressed in *Escherichia coli*, and its purification and enzymatic characterization," Protein Expression and Purification 46 (2006) 248-255.
Inouye, K et al., "Sodium chloride enhances markedly the thermal stability of thermolysin as well as its catalytic activity," Biochimica et Biophysica Acta 1388 (1998) 209-214.
Latt, S: et al., "Thermolysin: A Zinc Metalloenzyme," Biochemical and Biophysical Research Communications 37:2 (1969) 333-339.
Marie-Claire, C. et al., "Intramolecular Processing of Prothermolysin," The Journal of Biological Chemistry 273:10 (Mar. 6, 1998) 5697-5701.

(Continued)

*Primary Examiner* — Rosanne Kosson

(57) ABSTRACT

The present invention deals with the proteolytic enzyme thermolysin which tends to be unstable in aqueous solution. The invention provides methods and compositions to enhance the stability of dissolved thermolysin in aqueous solution. Thermolysin, crude thermolysin or a lyophilisate containing thermolysin and one or more salts, is contacted with an aqueous buffer with a low salt concentration and a first solution is formed. Subsequently, a further salt in solid form is added and dissociated, thereby forming a second solution comprising thermolysin in a stabilized form.

8 Claims, 3 Drawing Sheets

OTHER PUBLICATIONS

Marie-Claire, C. et al., The Prosequence of Thermolysin Acts as an Intramolecular Chaperone when Expressed in trans with the Mature Sequence in *Escherichia coli*, JMB 285 (1999) 1911-1915.

Matsubara, H. et al., "Other Bacterial, Mold and Yeast Proteases," Enzymes 3 (1971) 721-795.

Morihara, K. et al., "Thermolysin: Kinetic Study with Oligopeptides," Eur. J. Biochem 15 (1970) 374-380.

Nakanishi, K. et al., "Continuous Peptide Synthesis in a Water-immiscible Organic Solvent with an Immobilized Enzyme," Annals New York Academy of Sciences 652-655, 1990.

O'Donohue, M. et al., "Cloning and expression in *Bacillus subtilis* of the npr gene from *Bacillus thermoproteolyticus* Rokko coding for the termostable metalloprotease thermolysin," Biochem. J. 300 (1994) 599-603.

O'Donohue M. et al., "The Roles of the Prosequence of Thermolysin in Enzyme Inhibition and Folding in Vitro," The Journal of Biological Chemistry 271:43 (Oct. 25, 1996) 26477-26481.

Ohta, Y. et al., "Thermostable Protease from Thermophilic Bacteria," The Journal of Biological Chemistry 241:24 (Dec. 25, 1966) 5919-5925.

Oyama, K. et al., "On the Mechanism of the Action of Thermolysin: Kinetic Study of the Thermolysin-catalysed Condensation Reaction of N-Benzyloxycarbonyl-L-aspartic Acid with L-Phenylalanine Methyl Ester," J.C.S. Perkin II (1981) 356-360.

Tajima, M. et al., "Role of Calcium Ions in the Thermostability of Thermolysin and *Bacillus subtilis* var. amylosaccharitiucus Neutral Protease," Fur. J. Biochem 64 (1976) 243-247.

Trusek-Holowina, A., "Synthesis of ZAIaPHeOMe, the precursor of bitter dipeptide in the two-phase ethyl acetate-water system catalysed by thermolysin," Journal of Biotechnology 102 (2003) 153-163.

\* cited by examiner

A

B

STABILIZATION OF THERMOLYSIN IN AQUEOUS SOLUTION

RELATED APPLICATIONS

This application claims priority to EP 08015100.4 filed Aug. 27, 2008.

FIELD OF THE INVENTION

The present invention pertains to the field of biochemistry. The present invention deals with the proteolytic enzyme thermolysin which tends to be unstable in aqueous solution. The invention provides methods and compositions to enhance the stability of dissolved thermolysin in aqueous solution. Thermolysin, crude thermolysin or a lyophilisate containing thermolysin and one or more salts, is contacted with an aqueous buffer with a low salt concentration and a first solution is formed. Subsequently, a further salt in solid form is added and dissociated, thereby forming a second solution comprising thermolysin in a stabilized form.

BACKGROUND OF THE INVENTION

Thermolysin [EC 3.4.24.27; CAS registry number 9073-78-3] is a thermostable neutral metalloproteinase (also referred to herein as "neutral protease") produced in the culture broth of Bacillus thermoproteolyticus (Endo, S., J., Ferment. Technol. 40 (1962) 346-353; Matsubara, H., Feder, J., in: 3rd ed., Boyer, P., D., (Ed.), The Enzymes, vol. 3, Academic Press, New York, 1971, pp. 721-795). It requires one zinc ion for enzyme activity and four calcium ions for structural stability (Latt, S., A., et al. Biochem. Biophys. Res. Commun. 37 (1969) 333-339; Feder, J., et al. Biochemistry 10 (1971) 4552-4556; Tajima, M., et al. Eur. J. Biochem. 64 (1976) 243-247) and catalyzes specifically the hydrolysis of peptide bonds containing hydrophobic amino acid residues (Morihara, K., Tsuzuki, H., Eur. J. Biochem. 15 (1970) 374-380; Inouye, K., et al. Biochem. J. 315 (1996) 133-138). Thermolysin is widely used for the peptide bond formation through reverse reaction of hydrolysis (Oyama, K., et al., J. Chem. Soc. Perkin 11 (1981) 356-360; Nakanishi, K., et al., Ann. N.Y. Acad. Sci. 613 (1990) 652-655; Trusek-Holownia, A., J. Biotechnol. 102 (2003) 153-163). The npr gene that encodes thermolysin was isolated from B. thermoproteolyticus (O'Donohue, M., J., et al., Biochem. J. 300 (1994) 599-603). Sequence analysis reveals that thermolysin is synthesized as a pre-proprotein consisting a signal peptide (28 residues), a prosequence (204 residues), and a mature sequence (316 residues) (O'Donohue, M., J., et al., supra). The prosequence acts as an intramolecular chaperone leading to an autocatalytic cleavage of the peptide bond linking the pro and mature sequences (O'Donohue, M., J., et al., J. Biol. Chem. 271 (1996) 26477-26481; Marie-Claire, C., et al., J. Biol. Chem. 273 (1998) 5697-5701; Marie-Claire, C., et al., J. Mol. Biol. 285 (1999) 1911-1915).

The theoretical extinction at 280 nm of intact thermolysin in water can be calculated using the "ProtParam tool" which is publicly available via the internet. ProtParam is a tool which allows the computation of various physical and chemical parameters for a given protein stored in Swiss-Prot or TrEMBL or for a user entered sequence. The computed parameters include the molecular weight, theoretical pI, amino acid composition, atomic composition, extinction coefficient, estimated half-life, instability index, aliphatic index and grand average of hydropathicity. Accordingly, the theoretical absorbance value in water of A (1 mg/ml), at 280 nm of 1.696 can be calculated.

The manufacturer of thermolysin (Daiwa Kasei K.K., Japan) referring to Ohta, Y et al. (J. Biol. Chem. 241 (1966) 5919-5925) indicates an absorbance of A (1 mg/ml), of 1.765 at 280 nm in 50 mM TrisHCl buffer, pH 7.

Inouye, K., et al. (J. Biochem. 123 (1998) 847-852) discloses an absorbance value A (1 mg/ml) of 1.83, determined at 277 nm and 25° C. for thermolysin Lot T8BA51 (Daiwa Kasei K.K., Osaka, Japan) in 10 mM $CaCl_2$, 40 mM TrisHCl, pH 7.5.

Thermolysin can be obtained as a lyophilisate from commercial suppliers. Daiwa Kasei K.K. (Japan) distributes a thermolysin with a molecular weight of 34,600 Da (Daltons), a pH optimum at pH 8.0, and a temperature optimum in the range of 65° C. and 70° C. According to the manufacturer, the enzyme is stable in a pH range of pH 5.0 and pH 8.5. A solubility of 0.02% in dilute buffer solution is indicated. Twice crystallized thermolysin can be purchased as a freeze-dried amorphous powder, wherein the enzyme protein in the dried matter is 60% [w/w] or higher. The dried matter additionally contains anhydrous calcium acetate (about 20% [w/w]) and anhydrous sodium acetate (about 10% [w/w]). For further crystallization the manufacturer describes a method comprising the steps of suspending the lyophilisate at a concentration in the range of 1% [w/v] and 5% [w/v] in an aqueous solution of 0.01 M. Calcium-acetate. The suspended material is dissolved by adding drop wise enough 0.2N sodium hydroxide under agitation to bring the pH of the aqueous solution to a value in the range of pH 11.0 and pH 11.4. After removal of any undissolved residue, the pH of the solution is adjusted to pH 6.0 with 0.2N acetic acid. The crystallization is usually complete in approximately 2 days. The whole process is performed at a temperature in the range of about 0° and 2° C.

Preparations of thermolysin are also available from Daiwa Kasei K.K. (Japan) under the trade name Thermoase.

EP 0 640 687 discloses an aqueous solution of 7 mM $CaCl_2$ and 1.75 M NaCl in which Thermoase was dissolved to result in a concentration of about 36 mg/ml. The purity of thermolysin in the dry Thermoase powder was about 20%. Taking purity into account, the concentration of thermolysin in the aqueous solution was about 7 mg/ml.

Inouye, K., et al. (J. Biochem. 123 (1998) 847-852) reported that thermolysin is a sparingly soluble protein. It was suggested that the surface of the protein is hydrophobic to a large extent and the fact that thermolysin can be purified efficiently by way of hydrophobic interaction chromatography supports this notion (Inouye, K., et al., Protein Expression and Purification 46 (2006) 248-255). As a consequence of its low solubility, the enzyme has a strong tendency to precipitate within hours from freshly prepared solutions.

Inouye, K. et al. (J Biochem. supra) further demonstrated that the solubility of thermolysin in an aqueous solvent can be increased if certain neutral salts are dissolved in the solvent when it is contacted with a lyophilized preparation of thermolysin. The effect was shown to be dependent on (1) temperature, (2) the particular neutral salt present in the solvent, and (3) the concentration of the respective neutral salt. In the document of Inouye, K. et al. (J. Biochem. supra) FIG. 2 discloses the results of a series of experiments in which an excessive amount of thermolysin lyophilized powder (three-times-crystallized-and-lyophilized preparation of thermolysin (Daiwa Kasei K.K., Osaka, Japan; Lot T8BA51; used without further purification) was mixed with a "standard buffer" (10 mM CaCl2, 40 mM TrisHCl, pH 7.5) which additionally contained a salt at a predetermined concentration (in the range of 0.5 M and 5 M). The concentration of dissolved protein was determined spectrophotometrically using an absorbance value, A (1 mg/ml), at 277 nm of 1.83 and a molecular mass of 34.6 kDa.

Tables 1-4 reproduce the approximate numerical values indicating the concentrations of dissolved protein as graphically depicted in FIG. 2 of Inouye, K. et al. (J. Biochem. supra), at two different temperatures (0° C. and 37° C.). The protein concentrations tabulated are in mg/ml. In each table the salts dissolved in the standard buffer are indicated as well as their respective concentrations.

TABLE 1

Concentrations of protein (in [mg/ml]) soluble at 0° C.
in standard buffer containing salt

| | | concentration of salt in standard buffer | | | | |
|---|---|---|---|---|---|---|
| | | 0.5 M | 1.0 M | 1.5 M | 2.0 M | 2.5 M |
| salt | NaCl | ~6.4 | ~8.9 | ~10.3 | ~12.2 | ~11.6 |
| | KCl | ~4.5 | ~6.3 | ~7.5 | ~6.5 | ~5.3 |
| | LiCl | ~1.9 | ~3.3 | ~4.5 | ~5.3 | ~6.6 |
| | NaBr | ~4.4 | ~6.6 | ~15.6 | ~25.3 | ~38.4 |
| | NaJ | ~5.5 | ~7.8 | ~20.3 | ~29.2 | ~32.5 |

TABLE 2

Concentrations of protein (in [mg/ml]) soluble at 0° C.
in standard buffer containing salt

| | | concentration of salt in standard buffer | | | | |
|---|---|---|---|---|---|---|
| | | 3.0 M | 3.5 M | 4.0 M | 4.5 M | 5.0 M |
| salt | NaCl | ~9.5 | ~8.1 | ~6.9 | ~5.3 | ~3.8 |
| | KCl | ~5.2 | ~4.4 | ~4.1 | ~3.4 | ~2.5 |
| | LiCl | ~8.0 | ~11.1 | ~14.7 | ~21.6 | ~26.3 |
| | NaBr | ~40 | ~36.6 | ~30 | ~27.8 | ~25.3 |
| | NaJ | ~34.4 | ~37.5 | ~38.6 | ~42.3 | § |

§ out of detection range

TABLE 3

Concentrations of protein (in [mg/ml]) soluble at 37° C.
in standard buffer containing salt

| | | concentration of salt in standard buffer | | | | |
|---|---|---|---|---|---|---|
| | | 0.5 M | 1.0 M | 1.5 M | 2.0 M | 2.5 M |
| salt | NaCl | ~2.7 | ~3.8 | ~5.5 | ~7.5 | ~8.8 |
| | KCl | ~1.6 | ~3.1 | ~3.2 | ~4.2 | ~3.4 |
| | LiCl | ~0.9 | ~2.2 | ~2.5 | ~3.1 | ~4.5 |
| | NaBr | ~3.4 | ~5.0 | ~9.7 | ~13.3 | ~18 |
| | NaJ | ~3.4 | ~6.2 | ~18 | ~24.5 | ~34.4 |

TABLE 4

Concentrations of protein (in [mg/ml]) soluble at 37° C.
in standard buffer containing salt

| | | concentration of salt in standard buffer | | | | |
|---|---|---|---|---|---|---|
| | | 3.0 M | 3.5 M | 4.0 M | 4.5 M | 5.0 M |
| salt | NaCl | ~7.4 | ~5.5 | ~3.1 | ~2.3 | ~1.0 |
| | KCl | ~3.1 | ~2.8 | ~2.2 | ~1.9 | ~0.6 |
| | LiCl | ~7.0 | ~8.8 | ~11.3 | ~18 | ~22.3 |
| | NaBr | ~22.2 | ~24.4 | ~26.3 | ~29 | ~33.1 |
| | NaJ | ~36.7 | ~38.1 | ~35.3 | ~38.6 | ~38.0 |

Accordingly, for selected salts the highest concentrations of soluble protein were each about

| 8.8 mg/ml | at 37° C. | in the presence of | 2.5 M | NaCl, |
| 12.2 mg/ml | at 0° C. | in the presence of | 2 M | NaCl, |
| 4.2 mg/ml | at 37° C. | in the presence of | 2 M | KCl, |
| 7.5 mg/ml | at 0° C. | in the presence of | 1.5 M | KCl, |
| 22.3 mg/ml | at 37° C. | in the presence of | 5 M | LiCl, |
| 26.3 mg/ml | at 0° C. | in the presence of | 5 M | LiCl, |
| 33.1 mg/ml | at 37° C. | in the presence of | 5 M | NaBr, |
| 40 mg/ml | at 0° C. | in the presence of | 3 M | NaBr, |
| 38.6 mg/ml | at 37° C. | in the presence of | 4.5 M | NaJ, and |
| >45 mg/ml | at 0° C. | in the presence of | 5 M | NaJ. |

Thermolysin is an aggressive protease which in solution undergoes autoproteolytic attack. Thus, both crystallized and freeze-dried preparations of thermolysin as well as solutions of such preparations contain amounts of different autoproteolytic fragments of thermolysin.

In order to limit autoproteolytic attack, low temperatures are applied to solutions containing thermolysin. However, enzymatic activity is only reduced (i.e. some proteolytic activity is still present) under such conditions, and not brought to a complete halt. In this regard it is noted that Inouye, K. et al, (J. Biochem. supra) determines protein content of solutions without any purification step. The protein concentrations detected therefore correspond to mixtures of intact thermolysin and degradation fragments thereof.

In view of the state of the art it is an object of the present invention to provide methods and compositions with a stabilized form of thermolysin in an aqueous solution. By providing a stabilized form, the tendency of thermolysin to precipitate is reduced, and solutions of the enzyme remain in a homogeneous state for a prolonged time.

The inventors have unexpectedly found that by dissolving thermolysin first in a buffer with a low ion concentration and then adding a salt and dissolving the salt in the solution which already contains thermolysin surprisingly allows to form a solution with a high concentration of thermolysin. At the same time, under such conditions according to the invention dissociated thermolysin is stabilized in the solution, i.e. the solution remains clear for an increased amount of time during which no precipitate is formed.

The invention provides significant benefit when amounts of thermolysin have to be kept in solution for dispensing aliquots thereof, or for making blends with preparations of other enzymes, such as collagenase enzymes. Such blends of proteolytic enzymes are of particular use in the dissociation of organ tissue for the separation of subsets of cells from the tissue.

SUMMARY OF THE INVENTION

A first aspect of the invention is a method for preparing a solution of thermolysin (EC 3.4.24.27) in which the dissolved thermolysin is in a stabilized form, the method comprising the first step (P) of mixing a solid preparation comprising thermolysin with an aqueous solvent and making a first solution, wherein the first solution comprises (i) a buffer salt capable of maintaining a pH in the range of pH 4.5 and pH 9, (ii) one or more salts, and (iii) thermolysin, and in the first solution the aggregate concentration of the one or more salts including the buffer salt or salts is in the range of about 0.1 mM and about 150 mM, wherein the method further comprises the subsequent step (Q) of adding to the first solution a measured amount of a further salt, whereby the salt is selected from the group consisting of NaCl, NaBr, $NaNO_3$, NaJ, KCl, LiCl, $MgCl_2$, $CaCl_2$, and a mixture thereof, and dissolving the further salt, thereby preparing a second solution in which the dissolved thermolysin is in a stabilized form.

Another aspect of the invention is a liquid composition comprising water, thermolysin in a dissociated form, a dissociated buffer salt capable of maintaining a pH in the range of pH 4.5 and pH 9, and a dissociated salt selected from the group consisting of NaCl, NaBr, $NaNO_3$, NaJ, KCl, LiCl, $MgCl_2$, $CaCl_2$, and a mixture thereof, wherein the composition is a homogeneous solution for five hours or more, and the composition contains thermolysin at a concentration in the range of about 1 mg/ml and about 10 mg/ml.

A further aspect of the invention is a liquid composition comprising water, thermolysin in a dissociated form, a dissociated buffer salt capable of maintaining a pH in the range of pH 4.5 and pH 9, and a dissociated salt selected from the group consisting of NaCl, NaBr, $NaNO_3$, NaJ, LiCl, $MgCl_2$, $CaCl_2$, and a mixture thereof, wherein the composition is a homogeneous solution for five hours or more, and the composition contains thermolysin at a concentration in the range of about 10 mg/ml and about 23 mg/ml.

Yet, another aspect of the invention is the use of a composition according to the invention for storage, transport, or dispensing of thermolysin in dissociated form.

DETAILED DESCRIPTION OF THE INVENTION

Figure 1:
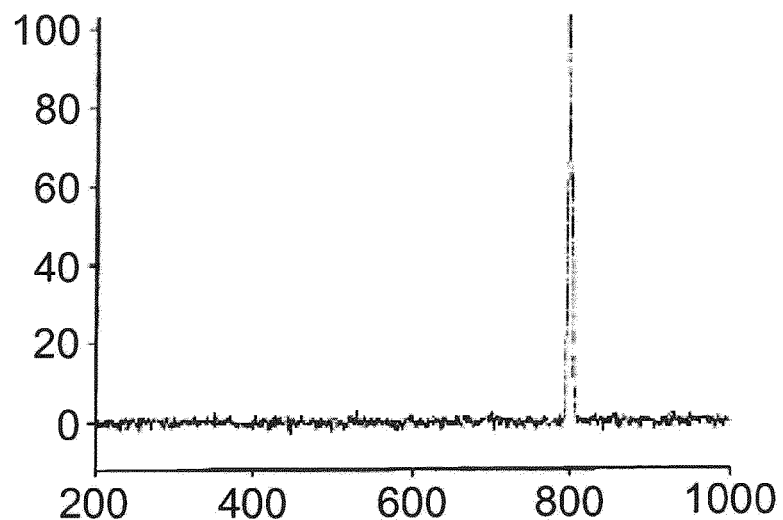
FIG. 1 Results of a wavelength scan as described in Example 8. The ordinate indicates light intensity in arbitrary units (a.u.) measured by the detector at 800 nm. The abscissa indicates the wavelength of the incoming light. (A) liquid sample containing the aqueous buffer; (B) liquid sample containing the colloid of thermolysin in the aqueous buffer.
Figure 1:
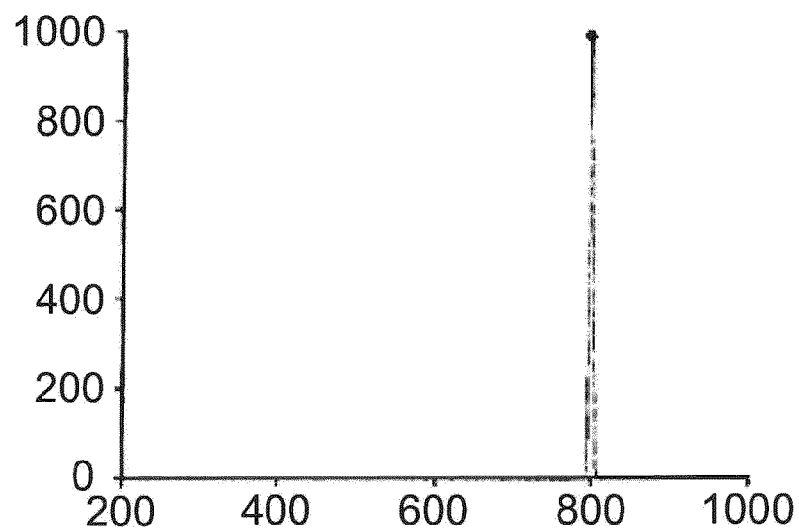

Certain terms are used with particular meaning, or are defined for the first time, in this description of the present invention. For the purposes of the present invention, the terms used are defined by their art-accepted definitions, when such exist, except that when those definitions conflict or partially conflict with the definitions set forth below. In the event of a conflict in definition, the meaning of a term is first defined by any of the definitions set forth below.

The term "comprising" is used in the description of the invention and in the claims to mean "including, but not necessarily limited to".

The articles "a" and "an" are used herein to refer to one or to more than one (i.e. to at least one) of the grammatical object of the article. By way of example, "a compound" means one compound or more than one compound.

When designating a range of numerical values such as, but not limited to, a concentration range, the range is indicated by a first value n1 and a second value n2 (e.g. "a range of n1 and n2"). The lower boundary of the designated range is understood as being the value equal to or higher than the first value. The higher boundary of the designated range is understood as being the value equal to or lower than the second value. Thus, a value x in the designated range is given by $n1 \leq x \leq n2$. When a range is indicated using the word "between", the upper and the lower boundary are understood as being included in the interval. Thus; the expression "a value x between n1 and n2" is understood as $n1 \leq x \leq n2$.

If not stated otherwise, it is understood that the term "about" and the character "~" in combination with a numerical value n ("about n", "~n") indicates a value x in the interval given by the numerical value±5% of the value, i.e. $n-0.05*n \leq x \leq n+0.05*n$. In case the term "about" or the character "~" in combination with a numerical value n describes a preferred embodiment of the invention, the value of n is most preferred, if not indicated otherwise.

A "mixture" is a substance made by combining two or more different materials with no chemical reaction occurring. The objects do not bond together in a mixture. A mixture can usually be separated back into its original components. Mixtures are the product of a mechanical blending or mixing of chemical substances like elements and compounds, without chemical bonding or other chemical change, so that each ingredient substance retains its own chemical properties and makeup. While there are no chemical changes in a mixture, physical properties of a mixture, such as its melting point, may differ from those of its components. Mixtures are either homogeneous or heterogeneous.

Homogeneous mixtures are mixtures that have definite, consistent properties. Particles are uniformly spread. For example, any amount of a given mixture has the same composition and properties. A homogeneous mixture is a uniform mixture consisting of only one phase. For the purpose of the invention, solutions of one or more dissociated salts are non-limiting examples for homogeneous mixtures.

A solution is a homogeneous mixture of one or more substances (the solutes) dissolved (i.e. dissociated) in another substance (the solvent). A common example would be a solid dissolving into a liquid (i.e. salt or protein dissolving in water). Solubility is a compound property. Depending on the conditions, the amount of a substance that can dissolve in a solvent or a solution can be variable.

Non-limiting examples for non-homogeneous (heterogeneous) mixtures are a colloid and a suspension. In the context of the invention, a suspension is understood as being a heterogenous fluid containing solid particles that are sufficiently large for sedimentation. Unlike colloids, the suspended particles settle over time if left undisturbed. This distinguishes a suspension from a colloid in which the suspended particles are smaller and do not settle.

In a solution, the dissolved substance does not exist as a solid, and solute(s) and solvent are homogeneously mixed. The term "stability" of a solution refers to the tendency of the dissolved substance to remain in the dissolved state. That is to say, the term refers to the ability of the solution to remain homogeneous during a given time interval. Stability can therefore be characterized in a quantifying way by determining said time interval. Thus, the dissolved substance in a first solution characterized by a lower stability exhibits a higher tendency to precipitate or form a colloid or a suspension, as opposed to a second solution characterized by a higher stability in which said tendency is lower. As a consequence, after a certain amount of time said first solution becomes a heterogeneous mixture whereas said second solution remains a homogeneous mixture.

Under certain conditions the stability of a solution can be increased, that is to say the tendency of a dissolved substance to precipitate is reduced. For the purpose of the present invention, a substance with a reduced tendency to precipitate is referred to as being in "a stabilized form".

Turbidity is a measure of water cloudiness caused by the presence of particles in a suspension or a colloid. There are several practical ways of determining turbidity, the most direct being some measure of attenuation (that is, reduction in strength) of light as it passes through a sample column of water. Thus, one way to determine turbidity is visual inspection, i.e. inspection by eye.

Another way of determination is measurement of light attenuation with a photometer. In this regard, the term "Optical density" (also referred to as "OD") denotes a unitless measure of the transmittance of an optical element for a given length at a given wavelength λ:

$$OD_{80} = \log_{10} O = -\log_{10} T = -\log_{10}(I/I_0)$$

whereby
O=the per-unit opacity
T=the per-unit transmittance
$I_0$=the intensity of the incident light beam.
I=the intensity of the transmitted light beam.

The higher the optical density, the lower the transmittance. Owing to the scattering of a light beam focused on the particles the optical density of a suspension or a colloid is increased compared to a clear solution.

A preferred way to determine turbidity is to measure the scattered light. To this end, a light scattering photometer is used frequently. Depending on the direction from which light scatter is detected and quantified, there are several types of scattered light photometers known to the art. In principle, all can be used for quantitative assessment of turbidity in liquid samples. The term "light scatter" collectively includes both the scatter of light waves by particles in the sample, as well as reflection by particulate matter in the sample. Back Scatter is defined as less than 90°, toward the light source. Forward scatter is defined as less than 90° away from, or in the same general direction as the light source. A majority of turbidity units of measure used today are based on 90° side scatter measurement techniques.

The intensity of the scattered light depends on the amount of the non-dissolved (particulate) matter in the heterogeneous mixture and can be described by Formula 1:

$$F = I_0 \cdot \Phi \cdot (2.303 \cdot \epsilon \cdot c \cdot d) \qquad \text{(Formula 1)}$$

whereby
F is the intensity of the scattered light
$I_0$ is the intensity of the incoming light beam
$\Phi$ is the ratio of emitted versus absorbed photons
$\epsilon$ is the molar absorption coefficient of the particulate substance in the mixture
c is the amount of the particulate substance per volume of the liquid sample (heterogeneous mixture) in the cuvette
d is the thickness of the space in the cuvette For the purpose of the invention, 90° side scatter measurements are made with a fluorescence photometer to determine cloudiness of heterogeneous mixtures containing thermolysin as particulate matter. Typically, such mixtures are colloids.

"Crude thermolysin" in the sense of the invention is a protein mixture consisting mainly of substantially undegraded (=intact) thermolysin and additionally of degradation products, typically resulting from autoproteolytic attack. Usually, about 70% of crude thermolysin is found substantially undegraded, while about 24% of crude thermolysin consists of different degradation products which retain proteolytic activity (to different degrees), and about 6% are proteolytically inactive fragments and further impurities. Thermoase is a preparation of crude thermolysin which is used to exemplify the advantageous effects of the present invention. However, the present invention is not limited to the use of Thermoase preparations, and other preparations of the enzyme can be used to practice the invention.

Thermoase is a lyophilisate with a protein content which is in the range of about 30% [w/w] and about 35% [w/w]. The protein in the lyophilizate consists of "crude thermolysin".

From the state of the art it is known that solubility of thermolysin increases if a salt, preferably a dissociated neutral salt is present in the aqueous buffer to be used as solvent of dry thermolysin, or of a dry composition containing thermolysin. However, aqueous solutions of thermolysin are unstable in that the dissolved thermolysin undergoes a transition which reduces its solubility. The precise nature of the transition is unclear but one can reasonably speculate that amino acid residues of one or more hydrophobic domain(s) of thermolysin play a role in this process. Due to the transition, solubility of thermolysin decreases. As a result, a freshly prepared clear solution of the enzyme becomes opaque and a substantial portion of the protein eventually precipitates. An example for the lack of stability is given in Example 6, Tables 13 and 14, No. 1-3. Even at reduced concentrations of the lyophilisate and in the presence of about 1.1 M NaCl, thermolysin has a strong tendency to precipitate after being brought in solution.

The inventors have surprisingly found that the transition can be suppressed and thermolysin can be stabilized in solution. To this end, thermolysin, crude thermolysin or a lyophilisate containing thermolysin and one or more salts is contacted with an aqueous buffer with a low salt concentration to form a solution which is stable only for a short time interval. Subsequently, a further salt in solid form is added and dissociated in the solution afterwards. After this step thermolysin in solution is in a stabilized form which is characterized by a significantly reduced tendency to precipitate.

According to the invention, before the aqueous buffer with the low salt concentration is contacted with thermolysin, crude thermolysin or a lyophilisate containing thermolysin, the concentration of dissociated salts, including buffer salt, in the buffer is preferably lower than 150 mM, preferably in the range of 0.1 mM and 150 mM. Depending on the preparation of thermolysin, the salt concentration of the aqueous buffer increases to the extent of salt being present in the thermolysin containing solid preparation dissociated in the buffer.

The salt in solid form preferably is a neutral salt with the exception of an inorganic sulfate salt. A preferred solid salt is selected from the group consisting of NaCl, NaBr, NaNO$_3$, NaJ, KCl, LiCl, MgCl$_2$, CaCl$_2$, and a mixture thereof.

The first main step is the formation of a clear solution containing thermolysin. In case the preparation of thermolysin does not allow to form a homogeneously clear solution, an additional clearing step is necessary. For example, the solution can be cleared by way of filtration, centrifugation or equivalent means.

As the second main step, the salt in solid form has to be added to the freshly prepared clear solution of thermolysin. At a temperature in the range of about 2° C. and about 8° C. the salt in solid form is added preferably not more than 30 min after the clear solution of thermolysin is obtained. Shorter periods such as not more than 15 min, 10 min, and 5 min are more preferred.

Using in the thermolysin solution a total concentration in the range of about 1.5 M and 3.5 M of the dissociated salt, thermolysin in solution becomes stabilized and the solution remains a clear homogeneous mixture for up to 16 h or even longer.

Surprisingly, this solution can be even diafiltrated against a buffer with a lower salt concentration; in such a process the concentration of the dissociated salt which was added previously can be lowered (see Example 2). Diafiltration in this regard is a crossflow filtration process allowing for the transfer of low molecular weight species, water and/or solvents through a membrane without changing the solution volume. This process is used for purifying retained large molecular weight species (i.e. substantially intact thermolysin), while low molecular weight species including proteolytic fragments of thermolysin are removed. The procedure of diafiltration at the same time allows for buffer exchange, thereby simply changing the properties of a given solution prior to the diafiltration process.

Even under these conditions (i.e. during a diafiltration process) thermolysin remains in a stabilized form, that is to say thermolysin remains stably in solution. The same effect is observed for frozen thermolysin solutions according to the invention after thawing.

Therefore, the invention particularly provides the means; compositions and conditions to manipulate homogeneous solutions of thermolysin for an extended amount of time under reproducible conditions. This is particularly useful when thermolysin is blended with other enzymes or when thermolysin solutions are dispensed as aliquots, e.g. using automated devices.

Yet, in more detail, the present invention comprises the following items:

1. A method for preparing a solution of thermolysin (EC 3.4.24.27) in which the dissolved thermolysin is in a stabilized form, the method comprising the first step (P) of mixing a solid preparation comprising thermolysin with an aqueous solvent and making a first solution, wherein the first solution comprises
    (i) a buffer salt capable of maintaining a pH in the range of pH 4.5 and pH 9,
    (ii) one or more salts, and
    (iii) thermolysin,
   and in the first solution the aggregate concentration of the one or more salts including the buffer salt or buffer salts is in the range of about 0.1 mM and 500 mM, and
   wherein the method further comprises the subsequent step (Q) of adding to the first solution a measured amount of a further salt, whereby the salt is selected from the group consisting of NaCl, NaBr, NaNO$_3$, NaJ, KCl, LiCl, MgCl$_2$, CaCl$_2$, and a mixture thereof, and dissolving the further salt,
   thereby preparing a second solution in which the dissolved thermolysin is in a stabilized form.

2. The method according to item 1, wherein the first solution obtained in step (P) is a homogeneous solution.

3. The method according to any of the items 1 and 2, wherein in step (P) the aqueous solvent comprises water and a buffer salt.

4. The method according to any of the items 1 and 2, wherein in step (P) the solid preparation comprising thermolysin additionally comprises one or more salts.

5. The method according to item 4, wherein in step (P) the aqueous solvent is water.

6. The method according to any of the items 1 to 5, wherein in step (P) the solid preparation comprises thermolysin at a concentration of about 20% [w/w] or higher.

7. The method according to any of the items 1 to 5, wherein in step (P) the solid preparation comprises thermolysin at a concentration in the range of about 20% [w/w] and 100% [w/w], more preferred in the range of about 20% [w/w] and about 80% [w/w], and even more preferred in the range of about 20% [w/w] and about 60% [w/w].

8. The method according to item 6 or item 7, wherein in step (P) the solid preparation comprises thermolysin at a concentration in the range of about 20% [w/w] and about 50% [w/w], more preferred in the range of about 20% [w/w] and about 40% [w/w], and even more preferred in the range of about 20% [w/w] and about 30% [w/w].

9. The method according to item 8, wherein in step (P) the solid preparation comprises thermolysin at a concentration of about 20% [w/w].

10. The method according to any of the items 1 to 9, wherein in step (P) the concentration of the preparation comprising thermolysin in the aqueous solvent is in the range of about 1 mg/ml and about 100 mg/ml.

11. The method according to item 10, wherein in step (P) the concentration of the solid preparation is in the range of about 20 mg/ml and about 60 mg/ml, and more preferred in the range of about 25 mg/ml and about 50 mg/ml, and even more preferred about 30 mg/ml.

12. The method according to any of the items 1 to 11, wherein in step (P) the one or more salts (ii) in the first solution comprise a salt selected from the group consisting of NaCl, Na$_2$SO$_4$, and a combination thereof.

13. The method according to item 4, wherein in step (F) the one or more salts in the solid preparation comprising thermolysin are selected from the group consisting of NaCl, Na$_2$SO$_4$, and a combination thereof.

14. The method according to item 13, wherein in step (P) the solid preparation contains NaCl in the range of about 50% [w/w] and about 70% [w/w], and/or Na$_2$SO$_4$ in the range of about 0.5% [w/w] and about 7.5% [w/w], and more preferred the solid preparation contains NaCl in the range of about 60% [w/w] and about 65% [w/w], and/or Na$_2$SO$_4$ in the range of about 3% [w/w] and about 6% [w/w].

15. The method according to any of the items 12 to 14, wherein in step (P) the solid preparation contains crude thermolysin.

16. The method according to any of the items 1 to 15, wherein in step (P) the concentration of sulfate ions in the first solution is in the range of about 1 mM and about 10 mM, more preferred the concentration of sulfate ions in the first solution is about 5 mM.
17. The method according to any of the items 1 to 16, wherein in the subsequent step (Q) the further salt is added in solid form.
18. The method according to any of the items 1 to 17, wherein the total concentration of the further salt in the second solution obtained after step (Q) is in the range of about 1.5 M and about 5 M.
19. The method according to item 18, wherein the total concentration of the further salt in the second solution obtained after step (Q) is in the range of about 2 M and about 3.5 M.
20. The method according to item 19, wherein the total concentration of the further salt in the second solution obtained after step (Q) is in the range of about 2 M and about 2.5 M.
21. The method according to item 19, wherein the total concentration of the further salt in the second solution obtained after step (Q) is about 2.3 M.
22. The method according to any of the items 17 to 21, wherein the concentration of sulfate ions in the second solution obtained after step (Q) is lower than about 10 mM.
23. The method according to item 22, wherein the concentration of sulfate ions in the second solution obtained after step (Q) is in the range of about 1 mM and about 10 mM, more preferred in the range of about 1 mM and about 5 mM.
24. The method according to any of the items 1 to 23, wherein in the first solution obtained in step (P) the aggregate concentration of the one or more salts including the buffer salt or salts is in the range of about 100 mM and 500 mM, more preferred in the range of about 300 mM and 400 mM.
25. The method according to any of the items 1 to 24, wherein in step (P) the aqueous solvent comprises $Ca^{2+}$ ions.
26. The method according to item 25, wherein in the aqueous solvent the concentration of $Ca^{2+}$ ions is in the range of about 0.1 mM and about 10 mM, even more preferred in the range of about 1 mM and about 10 mM.
27. The method according to item 26, wherein in the aqueous solvent the concentration of $Ca^{2+}$ ions is about 5 mM.
28. The method according to any of the items 1 to 27, wherein in step (P) the aqueous solvent comprises a buffer salt at a concentration in the range of about 0.1 mM and about 100 mM, and more preferred in the range of about 1 mM and about 100 mM.
29. The method according to item 28, wherein in the aqueous solvent the concentration of the buffer salt is in the range of about 5 mM and about 50 mM.
30. The method according to item 29, wherein in the aqueous solvent the concentration of the buffer salt is in the range of about 15 mM and about 25 mM.
31. The method according to item 30, wherein in the aqueous solvent the concentration of the buffer salt is about 20 mM.
32. The method according to any of the items 28 to 31, wherein the buffer salt is selected from the group consisting of BES (N,N-Bis(2-hydroxyethyl)-2-aminoethanesulfonic acid), Tris (tris(hydroxymethyl)aminomethane), BisTris(Bis(2-hydroxyethyl)amino-tris(hydroxymethyl) methane), BisTris propane (1,3-bis(tris(hydroxymethyl) methylamino)propane), HEPES (N-(2-hydroxyethyl)-piperazine-N'-2-ethanesulfonic acid), MES (2-(N-morpholino)ethanesulfonic acid), MOPS (3-(N-morpholine)propanesulfonic acid), MOPSO (3-morpholino-2-hydroxypropanesulfonic acid), PIPES (Piperazine-1,4-bis(2-ethanesulfonic acid)), TAPS(N-Tris(hydroxymethyl)methyl-3-aminopropanesulfonic acid), TES (N-Tris(hydroxymethyl)methyl-2-aminoethanesulfonic acid), TEA (Triethanolamine), and Tricine (N-(2-Hydroxy-1,1-bis(hydroxymethyl)ethyl)glycine).
33. The method according to any of the items 1 to 32, wherein in step (P) the pH of the first solution is in the range of about pH 5.5 and about pH 8.5.
34. The method according to item 33, wherein the pH is about pH 7.5.
35. The method according to any of the items 1 to 34, wherein in the second solution obtained after step (Q) the concentration of substantially intact thermolysin is about 5 mg/ml or higher, and wherein the thermolysin in solution is in a stabilized form.
36. The method according to item 35, wherein in the second solution obtained after step (Q) the concentration of substantially intact thermolysin is about 5 mg/ml or higher, and lower than about 35 mg/ml.
37. The method according to item 35, wherein the further salt is selected from the group consisting of KCl, LiCl, NaCl, NaBr, NaJ, $NaNO_3$, $MgCl_2$, $CaCl_2$, and a mixture thereof.
38. The method according to item 37, wherein the concentration of thermolysin in a stabilized form is about 10 mg/ml or higher, and lower than about 35 mg/ml.
39. The method according to item 38, wherein the concentration of thermolysin in a stabilized form is about 20 mg/ml.
40. A liquid composition comprising water, thermolysin in a dissociated form, a dissociated buffer salt capable of maintaining a pH in the range of pH 4.5 and pH 9, and a dissociated salt selected from the group consisting of NaCl, NaBr, $NaNO_3$, NaJ, KCl, LiCl, $MgCl_2$, $CaCl_2$, and a mixture thereof, wherein the composition contains thermolysin at a concentration in the range of about 1 mg/ml and about 10 mg/ml.
41. A liquid composition comprising water, thermolysin in a dissociated form, a dissociated buffer salt capable of maintaining a pH in the range of pH 4.5 and pH 9, and a dissociated salt selected from the group consisting of NaCl, NaBr, $NaNO_3$, NaJ, LiCl, $MgCl_2$, $CaCl_2$, and a mixture thereof, wherein the composition is a homogeneous solution for five hours or more, and the composition contains thermolysin at a concentration in the range of about 10 mg/ml and about 23 mg/ml.
42. The liquid composition according either to item 40 or according to item 41, the liquid composition being obtainable by a method according to any of the items 1 to 39.
43. The liquid composition according to any of the items 40 to 42, wherein the dissociated thermolysin is in a stabilized form.
44. The liquid composition according to any of the items 40 to 43, wherein at a temperature in the range of about 2° C. and about 8° C. and at least five hours after formation of the composition the turbidity of the composition about equals the turbidity of a reference solution, whereby said reference solution is composed of the same dissociated ingredients at the same respective concentrations as in the composition according to any of the items 41 and 42, and whereby the reference solution lacks thermolysin or fragments thereof.
45. The liquid composition according to any of the items 40 to 44, obtained by a method according to any of the items 1 to 39 and incubated for at a temperature in the range of about 2° C. and about 8° C., said composition being a homogeneous solution in an incubation interval of 0-5 hours, even more preferred in an incubation interval of more than 5 hours.

46. The liquid composition according to any of the items 44 and 45, wherein the dissociated thermolysin is substantially intact.
47. The liquid composition according to any of the items 44 to 46, wherein at a temperature of in the range of about 2° C. and about 8° C. for at least five hours after formation of the composition the turbidity of the composition about equals the turbidity of a reference solution, whereby said reference solution is composed of the same dissociated ingredients at the same respective concentrations as in the composition according to any of the items 44 to 46, and whereby the reference solution lacks thermolysin or fragments thereof.
48. A liquid composition comprising water, thermolysin in a dissociated form, a dissociated buffer salt capable of maintaining a pH in the range of pH 4.5 and pH 9, and dissociated NaCl at a concentration below 500 mM, and wherein the composition contains thermolysin at a concentration in the range of about 1 mg/ml and about 10 mg/ml.
49. The liquid composition according to item 48, wherein the pH of the composition is in the range of pH 7 and pH 8, even more preferred at about pH 7.5.
50. The liquid composition according to any of the items 48 and 49, wherein the composition comprises $Ca^{2+}$ ions, more preferred $Ca^{2+}$ ions at a concentration in the range of about 0.1 mM and about 10 mM, and even more preferred in the range of about 1 mM and about 10 mM.
51. The liquid composition according to any of the items 48 to 50, wherein in the composition the aggregate concentration of the dissociated salts including the buffer salt or salts is in the range of about 400 mM and about 200 mM, and more preferred the aggregate concentration of the dissociated salts including the buffer salt or salts is about 200 mM.
52. The liquid composition according to any of the items 48 to 51, wherein in the composition the concentration of dissociated sodium ions is in the range of 100 mM and 250 mM, more preferred the concentration of dissociated sodium ions is in the range of 150 mM and 200 mM, and even more preferred the concentration of dissociated sodium ions is about 170 mM.
53. The liquid composition according to any of the items 48 to 52, wherein the conductivity of the composition is about 20 mS/cm.
54. The liquid composition according to any of the items 48 to 53, wherein in the composition the concentration of substantially intact thermolysin is in the range of 0.1 mg/ml and 10 mg/ml, more preferred in the range of 1 mg/ml and 7.5 mg/ml, and even more preferred between 1 mg/ml and 5 mg/ml, even more preferred 2.5 mg/ml or 5 mg/ml.
55. The liquid composition according to any of the items 48 to 54, the liquid composition being obtainable by the method according to any of the items 1 to 39, followed by a subsequent step of diafiltrating the second solution obtained after step (Q) against a diafiltration buffer containing a dissociated buffer salt capable of maintaining a pH in the range of pH 4.5 and pH 9, and dissociated NaCl at a concentration below 500 mM.
56. The liquid composition according to item 55, wherein the diafiltration buffer comprises $Ca^{2+}$ ions at a concentration in the range of about 0.1 mM and about 10 mM.
57. The liquid composition according to any of the items 55 and 56, wherein in the diafiltration buffer the aggregate concentration of dissociated salts including the buffer salt or salts is in the range of about 400 mM and about 200 mM, and more preferred the aggregate concentration of the dissociated salts including the buffer salt or salts is about 200 mM.
58. Use of a liquid composition according to any of the items 40 to 57 for storage, transport, or dispensing of thermolysin, whereby the thermolysin is in dissociated form.

The following examples and figures are provided to aid the understanding of the present invention, the true scope of which is set forth in the appended claims. It is understood that modifications can be made in the procedures set forth without departing from the spirit of the invention.

Example 1

Preparation of Mixtures of an Aqueous Buffer and Thermolysin from a Thermoase Preparation According to information provided by the manufacturer, about 60-65% [w/w] of the lyophilisate was NaCl. In addition, the lyophilizate contained about 5% [w/w] $Na_2SO_4$ (decahydrate). An amount in the range of about 30% [w/w] and about 35% [w/w] of the Thermoase lyophilisate used here as well in the Examples further below consisted of crude thermolysin (see also Example 2). All of the working steps described below were performed at a temperature of in the range of 2° C. and 8° C., if not indicated otherwise.

A volume of 8 l of the aqueous buffer (A) containing 2 M NaCl, 5 mM $CaCl_2$, 20 mM HEPES, pH 7.5 was prepared. An amount of 200 g dry Thermoase lyophilisate was mixed with the aqueous buffer and the mixture was stirred continuously. However, no homogeneous mixture was obtained, the mixture remained turbid and never became entirely clear. About 60 min following the addition of the lyophilisate, the mixture became increasingly opaque and thermolysin started to precipitate.

Surprisingly, formation of an inhomogeneous mixture as obtained with buffer (A) could be avoided by first dissolving the Thermoase preparation in a buffer with low ionic strength and adding salt only thereafter. Thus, in a first step a volume of 6.5 l of the aqueous buffer (B) containing 5 mM $CaCl_2$, 20 mM HEPES, pH 7.5 was prepared. An amount of 200 g dry Thermoase lyophilisate was dissolved in buffer (B) and a clear solution was obtained. Subsequently, as a second step, 935 g solid NaCl was added and dissolved in the solution. As a third step, the volume of the solution was adjusted to 8 l by adding a further volume of aqueous buffer (B) and mixing by stirring. A homogeneous solution was obtained.

Taking into account that about 60-65% [w/w] of the lyophilisate consists of NaCl, the final NaCl concentration in the solution was about 2.3 M. The final concentration of crude thermolysin in solution was in the range of about 7.5 mg/ml and 8.8 mg/ml corresponding to a concentration of substantially undegraded thermolysin of about 5.7 mg/ml (in the range of about 5.2 mg/ml and 6.1 mg/ml).

TABLE 5

Calculated concentrations of Thermoase ingredients in the solubilization process; first step: Thermoase lyophilizate dissolved in a volume of 6.5 l, prior to addition of solid NaCl

| Ingredient | Concentration |
| --- | --- |
| $CaCl_2$ | 5 mM |
| HEPES, pH 7.5 | 20 mM |
| NaCl | ~329 mM |
| $Na_2SO_4$ | ~5 mM |
| Salts and buffer salts | ~359 mM |
| Crude thermolysin | ~10 mg/ml |
| Intact thermolysin | ~7 mg/ml |

TABLE 6

Calculated concentrations of salts including buffer salts in the solubilization process; second step: 6.5 l volume, after addition of solid NaCl

| Ingredient | Concentration |
|---|---|
| $CaCl_2$ | ~5 mM |
| HEPES, pH 7.5 | ~20 mM |
| NaCl | ~2790 mM |
| $Na_2SO_4$ | ~5 mM |
| Salts and buffer salts | ~2820 mM |

TABLE 7

Calculated final concentrations of Thermoase and salt ingredients in the solubilization process; third step: volume adjusted to 8 l

| Ingredient | Concentration |
|---|---|
| $CaCl_2$ | 5 mM |
| HEPES, pH 7.5 | 20 mM |
| NaCl | ~2267 mM |
| $Na_2SO_4$ | ~4 mM |
| Salts and buffer salts | ~2296 mM |
| Crude thermolysin | ~8.1 mg/ml |
| Intact thermolysin | ~5.7 mg/ml |

Example 2

Stability of Solutions of Thermolysin with a Reduced NaCl Concentration

Firstly, a solution of Thermoase lyophilisate was prepared using buffer (B) and the three-step procedure as described in Example 1. In a subsequent step, the solution was diafiltrated, wherein the buffer of the liquid composition was changed to 20 mM HEPES, 5 mM $CaCl_2$, 170 mM NaCl, pH 7.5. Surprisingly, thermolysin remained stabilized, i.e. the diafiltrated solution remained homogeneous for 5 hours and even longer than 5 hours.

HPLC analysis of the solution of the Thermoase lyophilisate was performed before and after diafiltration using HPLC with a SUPERDEX 75 pg 10 mm/300 mm GL column (GE Healthcare Bio-Sciences AB) as the stationary phase. The mobile phase was an aqueous buffer containing 200 mM NaCl, 1 mM $CaCl_2$, 50 mM HEPES, pH 7.5. Sample volumes were 50 µl each. The flow rate was 0.5 ml/min, each HPLC run was performed for 80 min. The detection unit was a UV-Vis absorbance detector operated at 280 nm.

Figure 2:
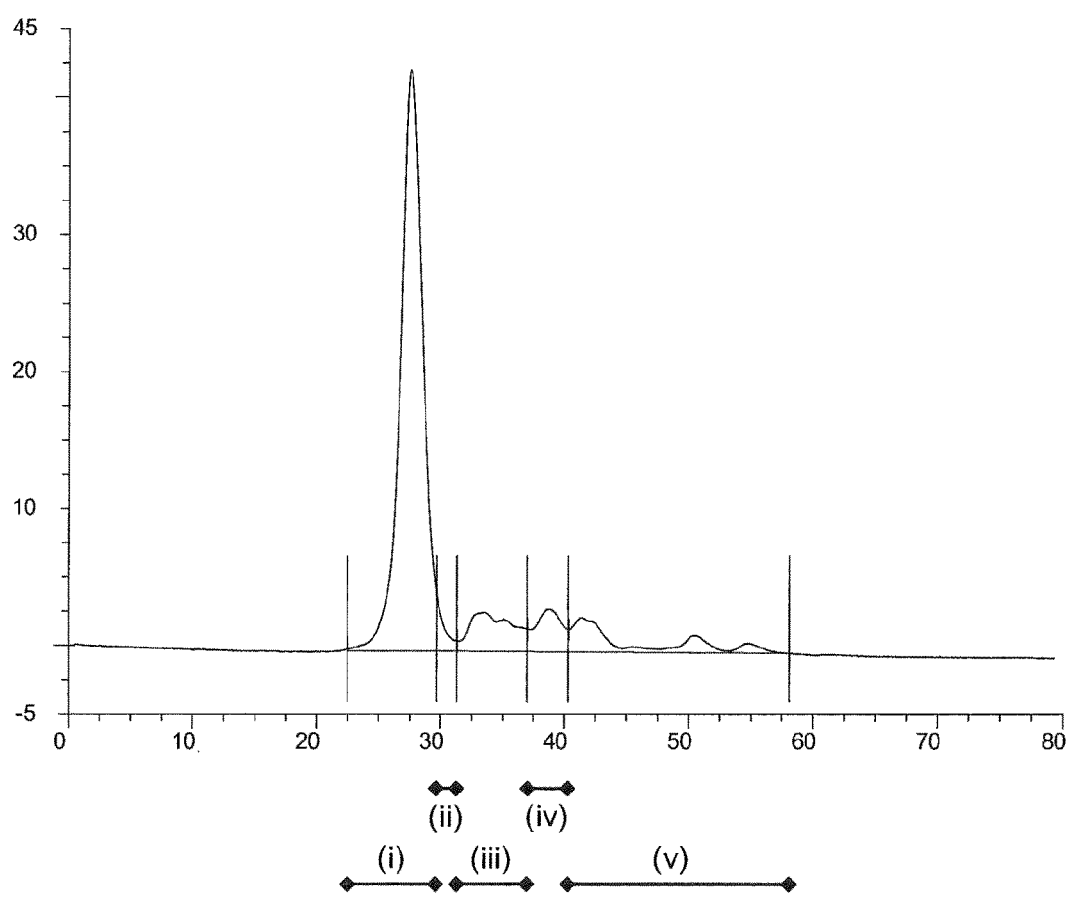
FIG. 2 Exemplary result of a chromatographic analysis of a solution containing Thermoase lyophilisate obtained from the first step described in Example 2, i.e. without/prior to a further diafiltration step. Thermoase lyophilisate was dissolved in an aqueous buffer containing 2.3 M NaCl, 5 mM $CaCl_2$, 20 mM HEPES, pH 7.5; the protein content of the solution was 8.2 mg/ml as determined photometrically at 280 nm. The Figure shows a HPLC chromatogram a 50 µl sample of the homogeneous solution. Five peak areas denoted (i) to (v) are marked. Conditions and parameters of HPLC are described in Example 2. Ordinate: mA.U.; abscissa: retention time in [min].
Figure 3:
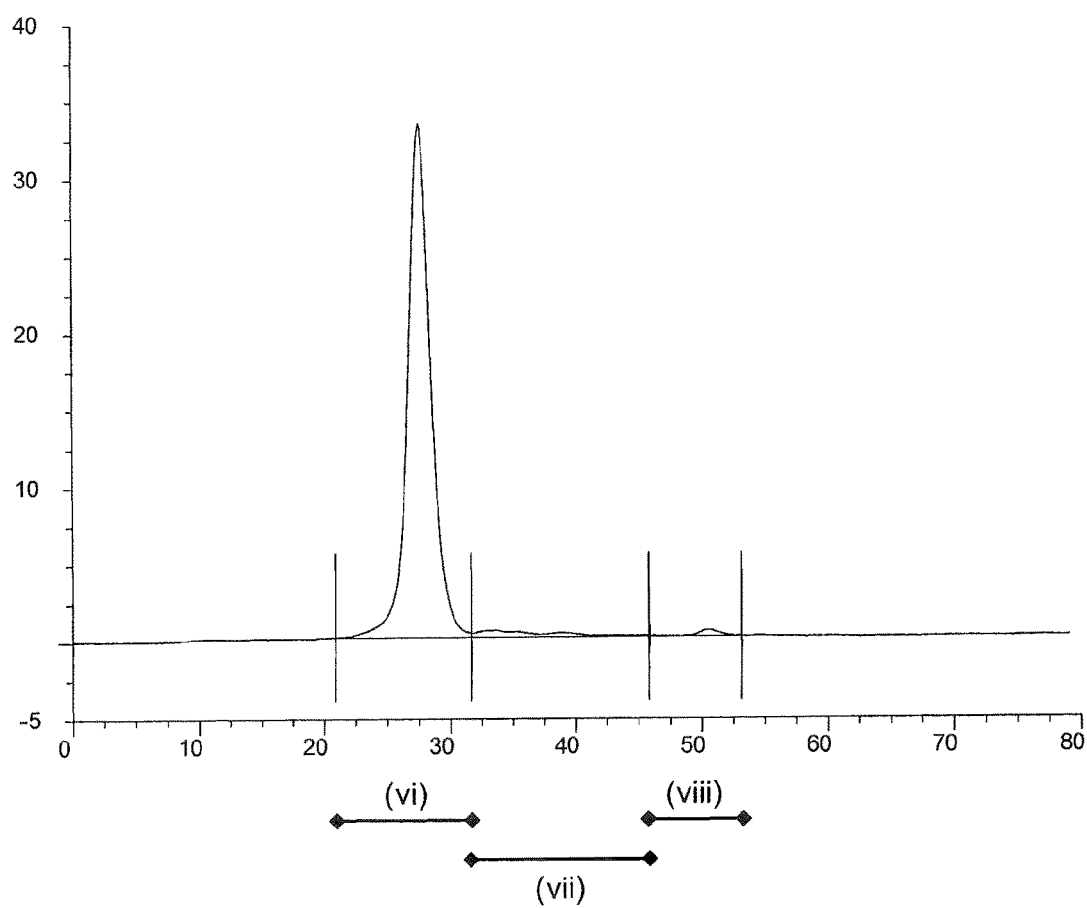
FIG. 3 Exemplary result of a chromatographic analysis of a solution containing Thermoase lyophilisate obtained from the second step described in Example 2, i.e. including/after the diafiltration step. Following diafiltration, thermoase was in an aqueous buffer containing 170 mM NaCl, 5 mM $CaCl_2$, 20 mM HEPES, 7.5; the protein content of the solution after diafiltration was 4.9 mg/ml as determined photometrically at 280 nm. The Figure shows a HPLC chromatogram a 50 µl sample of the homogeneous solution. Three peak areas denoted (vi) to (viii) are marked. Conditions and parameters of HPLC are described in Example 2. Ordinate: mA.U.; abscissa: retention time in [min].

In each sample the main peak eluted with a mean retention time of about 27 min 34 sec (see the peaks in area (i) shown in FIG. 2 and in area (vi) shown in FIG. 3).

Samples analyzed after the first step (no diafiltration) typically showed peaks that could be grouped into five different areas as shown in FIG. 2. The area under the main peak (denoted (i)) reflects substantially undegraded (=intact) thermolysin. The peak shoulder corresponding to elution after a retention time of about 20 min 15 sec was assumed to reflect thermolysin dimers. The peaks under the areas denoted (ii), (iii), and (iv) mainly corresponded to degradation products of thermolysin. Peaks under the area denoted (v) mainly reflected more (to different degrees) strongly degraded thermolysin fragments as well as impurities.

Samples analyzed after the second step, i.e. following diafiltration gave results as exemplarily shown in FIG. 3. Most notably, the relative amount of degradation fragments and impurities corresponding to the peak areas denoted (vii) and (viii) were reduced in diafiltrated preparations. In addition, the main peak in the area designated (vi) typically was much more distinct when compared with its counterpart in FIG. 2. Thus, the chromatogram after diafiltration indicated substantial separation and purification of undegraded thermolysin.

TABLE 8

Characterization of peaks and quantification of the peak areas of FIG. 2

| Peak area No. | Retention time [min] | Height [mA.U.] | Area [mA.U. * min] | Relative peak area [%] |
|---|---|---|---|---|
| (i) | 27.56 | 42.381 | 88.655 | 72.19 |
| (ii) | 31.33 | 0.679 | 2.658 | 2.16 |
| (iii) | 33.59 | 2.810 | 11.595 | 9.44 |
| (iv) | 38.60 | 3.074 | 7.692 | 6.26 |
| (v) | 41.27 | 2.479 | 12.201 | 9.94 |
| Σ | | 51.423 | 122.801 | 100.00 |

TABLE 9

Characterization of peaks and quantification of the peak areas of FIG. 3

| Peak area No. | Retention time [min] | Height [mA.U.] | Area [mA.U. * min] | Relative peak area [%] |
|---|---|---|---|---|
| (vi) | 27.57 | 33.257 | 71.322 | 95.01 |
| (vii) | 31.61 | 0.460 | 2.906 | 3.87 |
| (viii) | 50.39 | 0.418 | 0.837 | 1.11 |
| Σ | | 34.135 | 75.065 | 100.00 |

For further testing, two different stock solutions of thermolysin (i) 5 mg/ml and (ii) 2.5 mg/ml were prepared, whereby at both concentrations the aqueous buffer was adjusted to 20 mM HEPES, 5 mM $CaCl_2$, 170 mM NaCl, pH 7.5 by way of diafiltration; the conductivity of the buffer with the dissolved thermolysin was about 20 mS/cm. Both solutions were sterilized by sterile filtration and dispensed into aliquots.

From the time point when the lyophilisate was dissolved in the first aqueous buffer until the aliquots of the two stock solutions were obtained, thermolysin remained dissociated in solution for about 6 h. Both stock solutions remained clear throughout the process.

Additionally, an amount of 5 mg of Thermoase lyophilizate was dissolved in 1 ml of an aqueous buffer containing 1 mM $CaCl_2$ and 5 mM HEPES, pH 7.5. A 50 µl aliquot of the solution was analyzed by HPLC under standard conditions (see above) using a SUPERDEX 75 column 10/300, a pump speed of 0.5 ml/min and with UV/Vis detection at 280 nm. The mobile phase was 1 mM $CaCl_2$, 200 mM NaCl, 50 in M HEPES, pH 7.5 in water. The thermolysin peak was quantified relative to the other peaks obtained. Using this approach the relative amount of substantially intact thermolysin was determined in several lots of Thermoase. Four independent determinations indicated that on the average about 70% of the protein fraction of Thermoase was intact thermolysin. Individual values found were 59%, 72%, 71%, and 76%.

An exemplary amount of 100 g of Thermoase lyophilisate contained about 33 g of crude thermolysin, about 65 g of NaCl, and about 2 g of Na$_2$SO$_4$. Variation of protein content in Thermoase preparations was observed in the range of 30 g and 35 g per 100 g of lyophilizate. Typically, the fraction of substantially undegraded and enzymatically active thermolysin with a molecular weight of about 34,600 Da (also referred to as "thermolysin") was about 23% in the dry lyophilisate. The remaining amount of about 10% of protein in the dry lyophilisate mainly consisted of degradation products of thermolysin of which about 80% retained proteolytic activity. The remainder comprised more heavily degraded thermolysin fragments and other impurities. Therefore, "crude thermolysin" in the sense of the invention is understood as being a protein mixture consisting of (a) about 70% substantially undegraded thermolysin, (b) about 24% of thermolysin degradation products which retain proteolytic activity (to different degrees), and (c) about 6% of proteolytically inactive fragments and further impurities.

Example 3

Stability of Thermolysin Stock Solutions with a Reduced NaCl Concentration at Different Temperatures Aliquots of the two stock solutions of thermolysin with the concentrations of (i) 5 mg/ml and (ii) 2.5 mg/ml obtained according to the procedure of Example 2 (i.e. including diafiltration) were incubated at different temperatures. In intervals of 30 min turbidity was assessed by visual inspection and measurements as described in Example 9. The time of exposure to the respective temperature before a solution became turbid was recorded. The results are summarized in Table 10.

So far, all of the working steps were performed at 8° C. or lower, i.e. at temperatures in the range of 2° C. and 8° C. Both stock solutions remained clear throughout the process.

TABLE 10

Thermolysin concentrations, temperatures and time during which the thermolysin solution remained clear

| | Concentration of thermolysin in 20 mM HEPES, 5 mM CaCl$_2$, 170 mM NaCl, pH 7.5 | |
| --- | --- | --- |
| | 2.5 mg/ml | 5 mg/ml |
| Temp. | Time of permanency of homogeneous (clear) solution | |
| 0° C. | 21 h | 8 h |
| 2° C. | 21 h | 8 h |
| 4° C. | 21 h | 8 h |
| 6° C. | 21 h | 8 h |
| 8° C. | 21 h | 8 h |
| 10° C. | 21 h | 4 h |

Example 4

Stability of Solutions with a Thermolysin Concentration of 2.5 Mg/Ml after Freezing and Thawing After an incubation for 21 h at 4, 6, 8, and 10° C., aliquots containing 2.5 mg/ml (see Example 3) were frozen at −20° C. and stored at that temperature for 6 days. After thawing the aliquots were incubated at 8° C. The time of exposure to the temperature before a solution became turbid was recorded. The results are summarized in Table 11.

TABLE 11

Incubation temperatures before freezing and time after thawing during which the thermolysin solution remained clear

| Temp. before freezing | Time of permanency of homogeneous (clear) solution after thawing |
| --- | --- |
| 4° C. | 7 h |
| 6° C. | 6 h |
| 8° C. | 4 h |
| 10° C. | 1 h |

Example 5

Stability of Solutions with Different Concentrations of Thermolysin after Freezing and Thawing Stock solutions with thermolysin solutions in the range of 1 mg/ml and 5 mg/ml were prepared similarly as described in Example 2. Aliquots of the stock solutions were frozen at −20° C. and stored at that temperature for 7 days. After thawing the aliquots were incubated at 8° C. The time of exposure to the temperature before a solution became turbid was recorded. The results are summarized in Table 12.

TABLE 12

Thermolysin concentrations and time after thawing during which the thermolysin solution remained clear

| Concentration of thermolysin in 20 mM HEPES, 5 mM CaCl$_2$, 170 mM NaCl, pH 7.5 | | | | | |
| --- | --- | --- | --- | --- | --- |
| 1 mg/ml | 2 mg/ml | 2.5 mg/ml | 3 mg/ml | 4 mg/ml | 5 mg/ml |
| Time of permanency of homogeneous (clear) solution | | | | | |
| 27 h | 27 h | 27 h | 27 h | 7 h | 3.5 h |

Example 6

Stability of Solutions Containing Thermolysin in the Presence of Different Salts Thermoase lyophilisate was dissolved at concentrations of 100, 50, and 25 mg/ml in 20 mM HEPES, 5 mM CaCl$_2$ pH 7.5. Directly afterwards, a salt selected from the group consisting of Na$_2$SO$_4$, NaCH$_3$COO, NaCl, NaBr, NaNO$_3$, and NaJ was added and dissolved. As a control, no salt was added. Table 13 indicates the concentrations of the respective ions in the solutions, taking into account the amounts present in the lyophilisate. Note that the ions present in the HEPES buffer are not accounted for in the table.

TABLE 13

Solutions of thermolysin with different salts added

| No. | salt added | conc. lyophilisate in [mg/ml] | crude thermolysin in [mg/ml] | thermolysin in [mg/ml] | Na+ ~[M] | Cl− ~[M] | SO4²− ~[M] | CH3COO−, Cl−, Br−, NO3−, J− [M] |
|---|---|---|---|---|---|---|---|---|
| 1 | — | 100 | ~33 | ~23 | 1.125 | 1.122 | 0.006 | 0 |
| 2 |  | 50 | ~16.5 | ~11.5 | 0.562 | 0.566 | 0.003 | 0 |
| 3 |  | 25 | ~8.3 | ~5.8 | 0.281 | 0.288 | 0.002 | 0 |
| 4 | Na2SO4 | 100 | ~33 | ~23 | 5.125 | 1.122 | 2.006 | 0 |
| 5 |  | 50 | ~16.5 | ~11.5 | 4.562 | 0.566 | 2.003 | 0 |
| 6 |  | 25 | ~8.3 | ~5.8 | 4.281 | 0.288 | 2.002 | 0 |
| 7 | NaCH3COO | 100 | ~33 | ~23 | 3.125 | 1.122 | 0.006 | 2.0 |
| 8 |  | 50 | ~16.5 | ~11.5 | 2.562 | 0.566 | 0.003 | 2.0 |
| 9 |  | 25 | ~8.3 | ~5.8 | 2.281 | 0.288 | 0.002 | 2.0 |
| 10 | NaCl | 100 | ~33 | ~23 | 3.125 | 3.122 | 0.006 | 2.0 |
| 11 |  | 50 | ~16.5 | ~11.5 | 2.562 | 2.566 | 0.003 | 2.0 |
| 12 |  | 25 | ~8.3 | ~5.8 | 2.281 | 2.288 | 0.002 | 2.0 |
| 13 | NaBr | 100 | ~33 | ~23 | 3.125 | 1.122 | 0.006 | 2.0 |
| 14 |  | 50 | ~16.5 | ~11.5 | 2.562 | 0.566 | 0.003 | 2.0 |
| 15 |  | 25 | ~8.3 | ~5.8 | 2.281 | 0.288 | 0.002 | 2.0 |
| 16 | NaNO3 | 100 | ~33 | ~23 | 3.125 | 1.122 | 0.006 | 2.0 |
| 17 |  | 50 | ~16.5 | ~11.5 | 2.562 | 0.566 | 0.003 | 2.0 |
| 18 |  | 25 | ~8.3 | ~5.8 | 2.281 | 0.288 | 0.002 | 2.0 |
| 19 | NaJ | 100 | ~33 | ~23 | 3.125 | 1.122 | 0.006 | 2.0 |
| 20 |  | 50 | ~16.5 | ~11.5 | 2.562 | 0.566 | 0.003 | 2.0 |
| 21 |  | 25 | ~8.3 | ~5.8 | 2.281 | 0.288 | 0.002 | 2.0 |

Table 14 indicates, with respect of the mixtures given in Table 13, if and for how long a stable homogeneous (i.e. clear) solution was obtained. Turbidity was assessed by visual inspection and measurements as described in Example 9. The symbols presented in the table indicate as follows:

| assessment by visual inspection | | a.u., 90° side scatter measurement |
|---|---|---|
| {# # #} | opaque | 901->1000 (overflow) |
| {o o} | cloudy | 401-900 |
| {o} | slightly cloudy | 131-400 |
| { } | clear | 0-130 |

TABLE 14

Stability of solutions of thermolysin in the presence of different salts

| No. | salt added | [0.1 h] | [1 h] | [5 h] | [10 h] | [15 h] | [20 h] |
|---|---|---|---|---|---|---|---|
| 1 | — | {###} >1000 | {###} >1000 | {###} >1000 | {###} >1000 | {###} >1000 | {###} >1000 |
| 2 |  | {###} >1000 | {###} >1000 | {###} >1000 | {###} >1000 | {###} >1000 | {###} >1000 |
| 3 |  | {###} >1000 | {###} >1000 | {###} >1000 | {###} >1000 | {###} >1000 | {###} >1000 |
| 4 | Na2SO4 | {###} >1000 | {###} >1000 | {###} >1000 | {###} >1000 | {###} >1000 | {###} >1000 |
| 5 |  | {###} >1000 | {###} >1000 | {###} >1000 | {###} >1000 | {###} >1000 | {###} >1000 |
| 6 |  | {###} >1000 | {###} >1000 | {###} >1000 | {###} >1000 | {###} >1000 | {###} >1000 |
| 7 | NaCH3COO | {###} >1000 | {###} >1000 | {###} >1000 | {###} >1000 | {###} >1000 | {###} >1000 |
| 8 |  | {o} 150 | {o} 329 | {oo} 680 | {###} 958 | {###} >1000 | {###} >1000 |
| 9 |  | { } 82 | { } 85 | { } 113 | {o} 268 | {oo} 479 | {oo} 520 |
| 10 | NaCl | {###} 912 | {###} >1000 | {###} >1000 | {###} >1000 | {###} >1000 | {###} >1000 |
| 11 |  | { } 110 | { } 120 | { } 126 | {o} 189 | {o} 302 | {oo}/ 507 |

TABLE 14-continued

Stability of solutions of thermolysin in the presence of different salts

| No. | salt added | [0.1 h] | [1 h] | [5 h] | [10 h] | [15 h] | [20 h] |
|---|---|---|---|---|---|---|---|
| 12 | | { } 85 | { } 87 | { } 81 | { } 92 | { } 102 | { } 83 |
| 13 | NaBr | { } 110 | { } 116 | { } 114 | { } 95 | { } 104 | { } 112 |
| 14 | | { } 95 | { } 110 | { } 125 | { } 85 | { } 93 | { } 85 |
| 15 | | { } 88 | { } 100 | { } 79 | { } 87 | { } 106 | { } 102 |
| 16 | NaNO$_3$ | { } 75 | { } 85 | { } 103 | { } 102 | { } 88 | { } 86 |
| 17 | | { } 68 | { } 65 | { } 73 | { } 69 | { } 100 | { } 79 |
| 18 | | { } 88 | { } 59 | { } 100 | { } 67 | { } 95 | { } 86 |
| 19 | NaJ | { } 78 | { } 93 | { } 112 | { } 85 | { } 96 | { } 79 |
| 20 | | { } 112 | { } 105 | { } 126 | { } 102 | { } 98 | { } 115 |
| 21 | | { } 109 | { } 96 | { } 75 | { } 112 | { } 87 | { } 83 |

Results are tabulated as {visual assessment} and "numerical value" (a.u., 90° side scatter measurement)

Example 7

Stability of Solutions Containing Thermolysin in the Presence of Different Salts Thermoase lyophilisate was dissolved at concentrations of 100, 50, and 25 mg/ml in 20 mM HEPES, 5 mM CaCl$_2$ pH 7.5. Directly afterwards, a salt selected from the group consisting of KCl, NaCl, LiCl, MgCl$_2$, and CaCl$_2$ was added and dissolved. As a control, no salt was added. Table 15 indicates the concentrations of the respective ions in the solutions, taking into account the amounts present in the lyophilisate. Note that the ions present in the HEPES buffer are not accounted for in the table.

Table 16 indicates, with respect of the mixtures given in Table 15, if and for how long a stable homogeneous (i.e. clear, non-cloudy) solution of thermolysin was obtained. Turbidity was assessed by visual inspection and measurements as described in Example 9. The symbols presented in the table indicate as follows:

| assessment by visual inspection | | a.u., 90° side scatter measurement |
|---|---|---|
| {# # #} | opaque | 901->1000 (overflow) |
| {0 0} | cloudy | 401-900 |
| {o} | slightly cloudy | 131-400 |
| { } | clear | 0-130 |

TABLE 15

Solutions of thermolysin with different salts added

| | salt added | conc. lyophilisate in [mg/ml] | crude thermolysin in [mg/ml] | thermolysin in [mg/ml] | Na$^+$ ~[M] | Cl$^-$ ~[M] | SO$_4^{2-}$ ~[M] | K$^+$, Li$^+$, Mg$^{++}$, Ca$^{++}$ [M] |
|---|---|---|---|---|---|---|---|---|
| 22 | — | 100 | 33 | 23 | 1.125 | 1.122 | 0.006 | 0 |
| 23 | | 50 | 16.5 | 11.5 | 0.562 | 0.566 | 0.003 | 0 |
| 24 | | 25 | 8.3 | 5.8 | 0.281 | 0.288 | 0.002 | 0 |
| 25 | KCl | 100 | 33 | 23 | 1.125 | 3.122 | 0.006 | 2.0 |
| 26 | | 50 | 16.5 | 11.5 | 0.562 | 2.566 | 0.003 | 2.0 |
| 27 | | 25 | 8.3 | 5.8 | 0.281 | 2.288 | 0.002 | 2.0 |
| 28 | NaCl | 100 | 33 | 23 | 3.125 | 3.122 | 0.006 | 2.0 |
| 29 | | 50 | 16.5 | 11.5 | 2.562 | 2.566 | 0.003 | 2.0 |
| 30 | | 25 | 8.3 | 5.8 | 2.281 | 2.288 | 0.002 | 2.0 |
| 31 | LiCl | 100 | 33 | 23 | 1.125 | 3.122 | 0.006 | 2.0 |
| 32 | | 50 | 16.5 | 11.5 | 0.562 | 2.566 | 0.003 | 2.0 |
| 33 | | 25 | 8.3 | 5.8 | 0.281 | 2.288 | 0.002 | 2.0 |
| 34 | MgCl$_2$ | 100 | 33 | 23 | 1.125 | 5.122 | 0.006 | 2.0 |
| 35 | | 50 | 16.5 | 11.5 | 0.562 | 4.566 | 0.003 | 2.0 |
| 36 | | 25 | 8.3 | 5.8 | 0.281 | 4.288 | 0.002 | 2.0 |
| 37 | CaCl$_2$ | 100 | 33 | 23 | 1.125 | 5.122 | 0.006 | 2.0 |
| 38 | | 50 | 16.5 | 11.5 | 0.562 | 4.566 | 0.003 | 2.0 |
| 39 | | 25 | 8.3 | 5.8 | 0.281 | 4.288 | 0.002 | 2.0 |

TABLE 16

Stability of solutions of thermolysin after different salts added

| salt added | [0.1 h] | [1 h] | [5 h] | [10 h] | [15 h] | [20 h] |
|---|---|---|---|---|---|---|
| 22 — | {###} >1000 | {###} >1000 | {###} >1000 | {###} >1000 | {###} >1000 | {###} >1000 |
| 23 | {###} >1000 | {###} >1000 | {###} >1000 | {###} >1000 | {###} >1000 | {###} >1000 |
| 24 | {###} >1000 | {###} >1000 | {###} >1000 | {###} >1000 | {###} >1000 | {###} >1000 |
| 25 KCl | {###} >1000 | {###} >1000 | {###} >1000 | {###} >1000 | {###} >1000 | {###} >1000 |
| 26 | {o} 250 | {o} 394 | {oo} 599 | {###} >1000 | {###} >1000 | {###} >1000 |
| 27 | { } 82 | { } 95 | { } 119 | {o} 269 | {oo} 708 | {###} 988 |
| 28 NaCl | {###} >1000 | {###} >1000 | {###} >1000 | {###} >1000 | {###} >1000 | {###} >1000 |
| 29 | { } 85 | { } 115 | { } 129 | {o} 189 | {o} 350 | {oo} 487 |
| 30 | { } 98 | { } 102 | { } 115 | { } 78 | { } 95 | { } 105 |
| 31 LiCl | { } 78 | { } 85 | { } 76 | { } 115 | { } 104 | { } 126 |
| 32 | { } 69 | { } 78 | { } 103 | { } 78 | { } 75 | { } 86 |
| 33 | { } 88 | { } 96 | { } 84 | { } 109 | { } 83 | { } 87 |
| 34 MgCl$_2$ | { } 102 | { } 85 | { } 78 | { } 96 | { } 109 | { } 76 |
| 35 | { } 96 | { } 86 | { } 87 | { } 79 | { } 115 | { } 78 |
| 36 | { } 84 | { } 76 | { } 95 | { } 88 | { } 94 | { } 117 |
| 37 CaCl$_2$ | { } 102 | { } 115 | { } 123 | { } 100 | { } 99 | { } 114 |
| 38 | { } 85 | { } 78 | { } 95 | { } 86 | { } 112 | { } 79 |
| 39 | { } 78 | { } 79 | { } 72 | { } 85 | { } 110 | { } 95 |

Results are tabulated as {visual assessment}/"numerical value" (a.u., 90° side scatter measurement)

Example 8

Determination of Turbidity

For the present invention, instrument-based observations of turbidity were made with a CARY ECLIPSE instrument (Varian, Inc. Palo Alto, Calif., USA).

Two liquid samples were provided, the first being a homogeneous aqueous buffer with 5 mM CaCl$_2$, 170 mM NaCl, 20 mM HEPES, pH 7.5 as dissolved ingredients; the second sample was a colloid consisting of the same buffer and additionally about 5 mg/ml thermolysin (also see Examples 2 and 3). Before measurements were taken, the colloid was allowed to form overnight at 10° C.

The parameter settings of the instrument were the following:

| | |
|---|---|
| Instrument: | Cary Eclipse |
| Instrument serial number | EL06033429 |
| Data Mode: | Fluorescence |
| Scan Mode | Emission |
| X mode | Wavelength (nm) |
| Start (nm) | 200 |
| Stop (nm) | 1000 |
| Ex. Wavelength (nm) | 800 |
| Ex. Slit (nm) | 5 |
| Em. Slit (nm) | 5 |
| Scan rate (nm/min) | 600 |
| Data interval (nm) | 1 |
| Averaging Time (s) | 0.1 |
| Excitation filter | Auto |
| Emission filter | open |
| PMT voltage (V) | medium |
| Corrected spectra | Off |
| Multicell holder | Multicell |
| Multi zero | Off |

Liquid samples were analyzed in standard quartz cuvettes. Both samples were characterized by way of a wavelength scan, whereby the wavelength of the incoming light was increased from 200 nm to 1,000 nm. The detection wavelength was kept constant at 800 nm. Neither fluorescence nor opalescence was detected. Scattered light was detected at the wavelength of the incoming light. Results are depicted in FIGS. 1 (A) and (B). For the clear buffer sample the measured intensity of scattered light was about 100 arbitrary units (a.u.). For the colloid of the second sample the scattered light created an overflow at the detector.

Example 9

Visual Inspection and Turbidity Measurements

For the demonstration of the effects of the present invention, instrument-based observations of turbidity were made with a CARY ECLIPSE instrument (Varian, inc. Palo Alto, Calif., USA). The wavelength of the incoming light was 800 nm; 90° side scatter was measured at the same wavelength (i.e. 800 nm). The parameter settings of the instrument were the following:

| | |
|---|---|
| Instrument: | Cary Eclipse |
| Instrument serial number | EL06033429 |
| Data Mode: | Fluorescence |
| Em. Wavelength (nm) | 800 |
| Ex. Wavelength (nm) | 800 |
| Ex. Slit (nm) | 5 |
| Em. Slit (nm) | 5 |
| Ave Time (sec) | 0.1 |
| Excitation filter | Auto |
| Emission filter | open |
| PMT voltage (V) | medium |
| Multicell holder | Multicell |
| Multi zero | Off |
| Replicates | 1 |
| Sample averaging | off |

Liquid samples were analyzed in standard quartz cuvettes.

Visual inspection of thermolysin containing liquid samples in test tubes was performed by grouping the samples into four categories: (i) "clear", (ii) "slightly cloudy", (iii) cloudy, (iv) "opaque". Thus, categories (ii) to (iv) reflected increasing degrees of turbidity. The categories were correlated with the readout of arbitrary units (a.u.) as indicated in Table 17.

TABLE 17

Turbidity of liquid samples, categories

| Category | Exemplary measured values | Value range for category |
|---|---|---|
| clear | 114; 85; 95 | 0-130 |
| slightly cloudy | 182; 188; 236; 248; 304; 297 | 131-400 |
| cloudy | 760; 783; 810; 815; 847 | 401-900 |
| opaque | ~1000; >1000 | 901->1000 (=overflow) |

For the purpose of the present invention, a "clear" thermolysin containing solution is characterized by a turbidity (determined as above) which is about equivalent to (i.e. about equals) the turbidity of a solution without thermolysin but otherwise with the same composition and concentrations of the respective ingredients. In line with the invention and as shown above, this corresponds to the range of 0 a.u. and 130 a.u., more preferred to the range of 50 a.u. and 130 a.u., determined as 90° side scatter using light with a wavelength of 800 nm under the conditions described above.

Example 10

Spectrophotometric Detection of Protein from Thermoase Preparation

All procedures prior to photometry were performed at ice-cold temperature. Thermoase was provided as freeze-dried amorphous powder (Daiwa Kasei K.K.). An amount of Thermoase lyophilizate was dissolved in aqueous Tris buffer containing 10 mM CaCl2, 40 mM TrisHCl, pH 7.5 to yield a solution of Thermoase lyophilizate with a concentration of 1 mg/ml.

As soon as a clear solution was obtained (assessed by visual inspection), photometric readings were taken at 277 nm and at 25° C.

Three different lots of Thermoase were analyzed repeatedly. Photometric readings ranged from 0.57 to 0.61. The potential impact of differences between A (1 mg/ml) values determined at 277 nm and 280 nm were assumed to be insignificant and smaller than other potential sources of error.

TABLE 18

Percentage [w/w] of protein (crude thermolysin) in Thermoase preparations using different A (1 mg/ml) values as reference

| Thermoase Lot | extinction at 277 nm (range) | A (1 mg/ml) 1.765 | 1.83 |
|---|---|---|---|
| 1 | 0.60-0.61 | 34%-35% | 33% |
| 2 | 0.57-0.59 | 32%-33% | 31%-32% |
| 3 | 0.58-0.60 | 33%-34% | 32%-33% |

What is claimed is:

1. A method for preparing a solution of stabilized thermolysin (EC 3.4.24.27), the method comprising:
   (a) the first step of mixing a solid preparation comprising thermolysin with an aqueous solvent and making a first solution, wherein the first solution comprises a first buffer salt capable of maintaining a pH in the range of 4.5 to 9, one or more second salts, and thermolysin, wherein in the first solution the aggregate concentration of the first and second salts is in the range of about 0.1 mM to 500 mM,
   (b) the second step of adding to the first solution a measured amount of a third salt, wherein the third salt is selected from the group consisting of NaCl, NaBr, NaNO$_3$, NaI, KCl, LiCl, MgCl$_2$, CaCl$_2$, and a mixture thereof, and
   (c) dissolving the third salt in the first solution, thereby obtaining a second solution in which the dissolved thermolysin is in a stabilized form.

2. The method according to claim 1, wherein in step (a) the solid preparation comprising thermolysin additionally comprises one or more fourth salts.

3. The method according to claim 1, wherein in step (a) the solid preparation comprises thermolysin at a concentration in the range of about 20% to 100% (w/w).

4. The method according to claim 1, wherein in step (a) the concentration of the preparation comprising thermolysin in the aqueous solvent is in the range of about 1 mg/ml to about 100 mg/ml.

5. The method according to claim 1, wherein the first solution comprises sulfate ions and wherein the concentration of the sulfate ions in the first solution obtained in step (a) is in the range of about 1 mM to about 10 mM.

6. The method according to claim 5, wherein the total concentration of the third salt in the second solution obtained after step (b) is in the range of about 2 M to about 3.5 M.

7. The method according to claim 1, wherein in the second solution obtained after step (b) the concentration of thermolysin is between about 5 mg/ml and than about 35 mg/ml.

8. The method according to claim 7, wherein in the second solution obtained after step (b) the concentration of thermolysin is between about 10 mg/ml and than about 35 mg/ml, and the third salt in step (b) is selected from the group consisting of NaCl, NaBr, NaNO$_3$, NaI, KCl, LiCl, MgCl$_2$, and CaCl$_2$.

* * * * *